(12) United States Patent
Hesl et al.

(10) Patent No.: US 9,169,972 B2
(45) Date of Patent: Oct. 27, 2015

(54) FORCE COMPENSATING DEVICE AND USE IN A MEDICAL SYSTEM

(71) Applicants: Stefan Hesl, Eschenbach (DE); Jürgen Plannerer, Kemnath (DE)

(72) Inventors: Stefan Hesl, Eschenbach (DE); Jürgen Plannerer, Kemnath (DE)

(73) Assignee: Siemens Aktiengesellschaft, München (DE)

( * ) Notice: Subject to any disclaimer, the term of this patent is extended or adjusted under 35 U.S.C. 154(b) by 218 days.

(21) Appl. No.: 13/855,461

(22) Filed: Apr. 2, 2013

(65) Prior Publication Data

US 2013/0279970 A1    Oct. 24, 2013

(30) Foreign Application Priority Data

Apr. 18, 2012   (DE) .......................... 10 2012 206 343

(51) Int. Cl.
  *F16F 1/14*      (2006.01)
  *F16P 3/00*      (2006.01)
  (Continued)

(52) U.S. Cl.
  CPC ................. *F16P 3/008* (2013.01); *A61B 6/447* (2013.01); *B66D 1/02* (2013.01); *F16M 2200/021* (2013.01); *F16M 2200/04* (2013.01); *Y10T 403/32254* (2015.01)

(58) Field of Classification Search
  CPC .............. B66D 1/02; B66D 5/00; F03G 1/08; F16F 15/30; B60T 1/005; B60T 1/067; B60G 2202/312; B60R 22/34; F16P 3/008; F16M 2200/021; F16M 2200/04
  USPC .......... 267/154, 160, 178; 188/69, 82.6, 82.7, 188/82.74; 242/372, 375, 375.1, 375.2, 242/375.3, 378, 382, 382.1, 382.5; 254/278, 334, 364
  See application file for complete search history.

(56) References Cited

U.S. PATENT DOCUMENTS 1,004,753 A * 10/1911 Doust ........................ 242/375.3
3,105,652 A    10/1963 Becker et al.
(Continued)

FOREIGN PATENT DOCUMENTS

CN       1332100 A    1/2002
DE    19747393 C2    11/1999
(Continued)

OTHER PUBLICATIONS

German Office Action dated Dec. 5, 2012 for corresponding German Patent Application No. DE 10 2012 206 343.9 with English translation.
(Continued)

*Primary Examiner* — Pamela Rodriguez
(74) *Attorney, Agent, or Firm* — Lempia Summerfield Katz LLC

(57) ABSTRACT

A force compensating device includes a force generating unit configured for generating a compensating force that at least partially counteracts a tractive force acting on the force compensating device. The device includes at least one safety unit that is rotatable about a first axis of rotation and which, in the event of a malfunction of the force generating unit, can be moved by the force generating unit from an operating position to a locked position. The safety unit includes a first element and a second element that are rotatably connected to each other at a second axis of rotation, and at least one locking unit that blocks rotational movement of the safety unit from the locked position back to the operating position when the safety unit has been triggered due to a malfunction. A two-part safety unit in combination with the locking unit allows the safety unit to trigger and remain triggered in all fault situations. The force compensating device may be used in a medical system.

20 Claims, 4 Drawing Sheets

(51) Int. Cl.
  *A61B 6/00* (2006.01)
  *B66D 1/02* (2006.01)

(56) References Cited

U.S. PATENT DOCUMENTS

| | | | |
|---|---|---|---|
| 3,384,321 A * | 5/1968 | Becker et al. | 242/375.1 |
| 5,899,401 A * | 5/1999 | Reimann et al. | 242/372 |
| 6,065,705 A | 5/2000 | Schmitt | |
| 6,379,042 B1 | 4/2002 | Polkus et al. | |
| 6,530,536 B2 | 3/2003 | Sumiyashiki et al. | |
| 7,410,151 B2 * | 8/2008 | Haupl et al. | 254/364 |
| 7,424,997 B2 * | 9/2008 | Achtari et al. | 254/278 |
| 7,854,551 B2 * | 12/2010 | Lv et al. | 378/189 |

FOREIGN PATENT DOCUMENTS

| | | |
|---|---|---|
| DE | 20112750 U1 | 2/2002 |
| DE | 102010055681 A1 | 6/2012 |

OTHER PUBLICATIONS

Chinese Office Action for Chinese Application No. 201310134501.4, dated Jul. 2, 2015, with English Translation.

* cited by examiner

FORCE COMPENSATING DEVICE AND USE IN A MEDICAL SYSTEM

RELATED APPLICATIONS

This application claims the benefit of German Patent Application No. DE 102012206343.9, filed Apr. 18, 2012, the entire contents of which are hereby incorporated herein by reference.

TECHNICAL FIELD

The present teachings relate generally to force compensating devices and methods for their use.

BACKGROUND

Oftentimes, when a mass is subject to pulling or holding actions, it is advantageous to compensate, at least partially, for the acting tractive forces.

For example, German utility model DE 201 12 750 U1 describes a cable rewind device for power-related garden and outdoor equipment that possesses a cable drum for rewinding a cable. The cable drum is subject to the load of a mainspring in the direction in which the cable is rewound. When the cable is unwound from the cable drum, the mainspring is tensioned. As a result, the cable unwound from the cable drum is constantly subject to a pulling force. This pulling force causes the cable to run in a straight direction from the electrically driven machine toward the cable collector. The cable collector can be mounted above the area to be operated on by the electrical machine (e.g., on a house wall). In the event of a breakage of the mainspring, it would be desirable for the cable collector to be blocked so that no more cable is released.

In another example, German patent specification DE 197 47 393 C2 describes a weight compensating apparatus that can be used for a medical device. The weight compensating apparatus has a cable drum that can be subjected to the force of a spiral spring element. The cable drum can receive a supporting cable capable of bearing a payload and has a safety device for triggering a locking device in the event that the spiral spring element breaks. Upon breakage of the spiral spring element, the outer end of the spiral spring element engages with a pawl of the locking device, which can be subjected to the force of a pawl spring in order to inhibit adjustability of the cable drum. The force of the pawl spring is such that the pawl does not release the locking of the cable drum during tensioning of the spiral spring element until a specific force is reached.

It has been found that a spring breakage pawl used as a safety device does not respond consistently in every fault situation. Although the safety device triggers momentarily under unfavorable conditions, it does not remain reliably pressed outward.

In short, it would be desirable to safely move a payload in an upward direction in the event of a broken spring. However, conventional approaches to solving this problem typically necessitate the application of considerable force.

SUMMARY AND DESCRIPTION

The scope of the present invention is defined solely by the appended claims, and is not affected to any degree by the statements within this summary.

By way of introduction, a force compensating device in accordance with the present teachings includes a force generating unit for generating a compensating force that at least partially counteracts a tractive force acting on the force compensating device.

In some embodiments, the force compensating device enables reliable triggering of a safety unit in the event of a malfunction.

In some embodiments, the force compensating device is used for counterbalancing a force exerted due to the weight of a component of a medical system.

DETAILED DESCRIPTION

Figure 1:
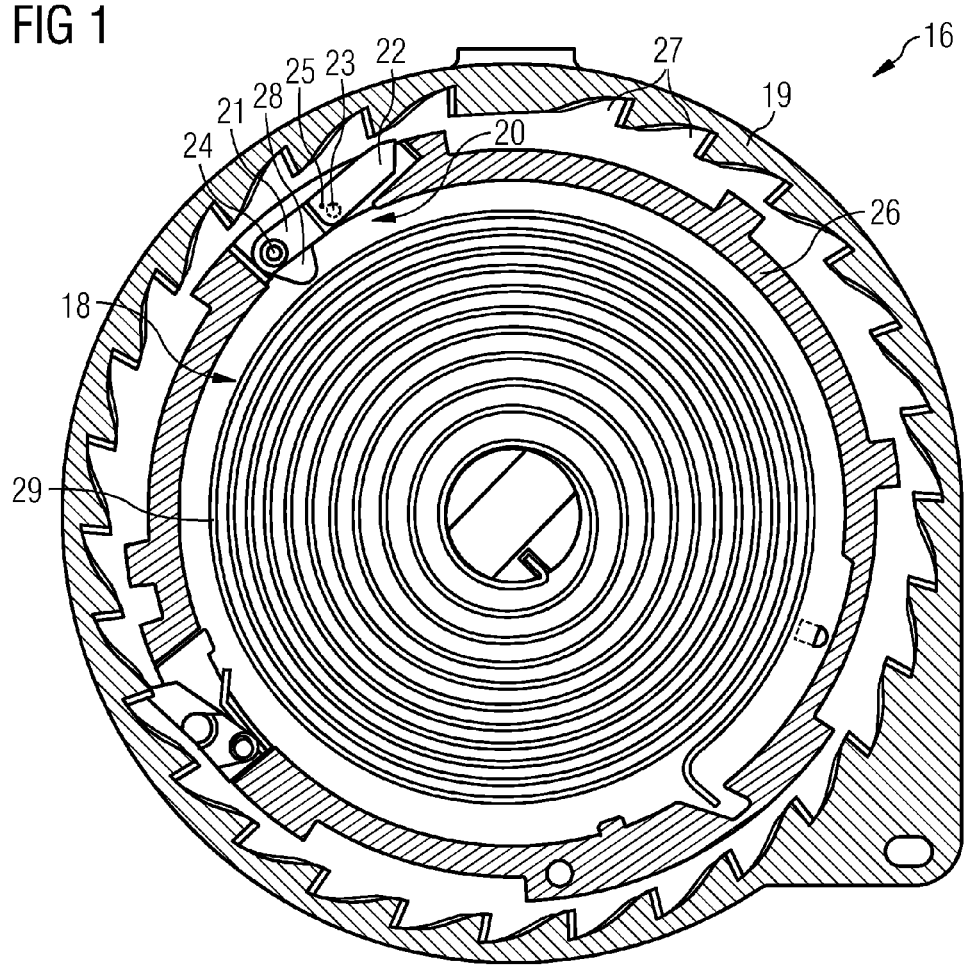
FIG. 1 shows a sectional view of a representative force compensating device that includes a spiral spring as a force generating unit.

By way of general introduction, a force compensating device in accordance with the present teachings prevents a movement in the direction of a tractive force in the event of a malfunction. This prevention is provided by a safety unit that fixes a force generating unit of the force compensating device in a locked position. A locking unit serves to prevent the safety unit from escaping from the locked position. In some embodiments, the safety unit is implemented in two parts in order to allow a movement in a direction counter to the direction of the tractive force.

In some embodiments, a force compensating device includes a force generating unit configured for generating a compensating force. The compensating force at least partially counteracts a tractive force that acts on the force compensating device. In some embodiments, the device includes at least one safety unit that is rotatable about a first axis of rotation. In the event of a malfunction of the force generating unit, the at least one safety unit may be moved by the force generating unit from an operating position to a locked position. In some embodiments, the safety unit includes a first element and a second element that are rotatably connected to each other at a second axis of rotation. In some embodiments, the safety unit further includes at least one locking unit configured to block a rotational movement of the safety unit from the locked position back into the operating position when the safety unit is triggered as the result of a malfunction.

In some embodiments, the use of a two-part safety unit in combination with the locking unit may offset problems that might otherwise result in unfavorable situations. For example, in a situation in which the locking unit does not trigger, the second element of the two-part safety unit can execute compensation movements independently of the first element, such that the locking unit triggers nonetheless. In addition, as a result of having the two-part safety unit, a movement counter to the tractive force (i.e., against the locking direction) can take place in spite of the locking unit being triggered.

In some embodiments, the safety unit may cause the compensating force to be equal to the tractive force at all times in the event of a malfunction. As a result, by way of example, a mass suspended from the force generating unit may be inhibited in its movement in the direction of the tractive force.

In some embodiments, the force compensating device includes at least one latching recess into which the safety unit engages in the locked position.

In some embodiments, the first element of the safety unit may be mounted around the first axis of rotation.

In some embodiments, the second element of the safety unit may engage into the latching recess.

In some embodiments, in the event of a malfunction, the force generating unit may move the first element of the safety unit around the first axis of rotation, such that the second element engages into the latching recess.

In some embodiments, in the event of a malfunction, the locking unit may block the second element of the safety unit in such a way that a return movement of the safety unit into the operating position is prevented.

In some embodiments, the force generating unit may include at least one spring element for generating the compensating force. In some embodiments, the spring element includes a spiral spring.

In some embodiments, the safety unit includes a two-part pawl.

In some embodiments, the locking unit includes a locking pin. In some embodiments, in the operating position of the safety unit, the locking pin is retained in a triggering position by the safety unit.

In some embodiments, the force compensating device includes a housing. In some embodiments, an inside face of the housing includes a latching recess.

In some embodiments, the tractive force may be a force exerted due to weight.

In some embodiments, a force compensating device in accordance with the present teachings is used for counterbalancing a force exerted due to the weight of a component of a medical system. In such embodiments, it is possible to prevent a component (e.g., a vertically movable x-ray tube assembly suspended from the ceiling) from falling onto a patient in the event of a malfunction.

Representative embodiments in accordance with the present teachings will now be described in reference to the appended drawings. The drawings and the description below have been provided solely by way of illustration, and are not intended to limit the scope of the appended claims or their equivalents.

FIG. 1 shows a sectional view of a representative force compensating device 16 that includes a spiral spring 18 as a force generating unit. The spiral spring 18 is arranged in a drum 26 that is rotatably mounted in a stationary housing 19. Latching recesses 27 are provided at regular intervals on the inside face of housing 19. A pawl 20 is arranged as a representative safety unit on the outer edge of drum 26. The pawl 20 includes a first element 21 and a second element 22. The first element 21 is rotatably connected to the drum 26 about a first axis of rotation 24. The two elements 21 and 22 are connected rotatably to each other about a second axis of rotation 25. The pawl 20 is located in an operating position in which the drum 26 may rotate freely. Located below pawl 20, at the level of the second element 22, is a locking pin 23 (shown in FIG. 1 by the dashed outline), which is provided as a representative locking unit. The locking pin 23 is tensioned by a spring (not shown) and presses onto pawl 20, such that when locking pin 23 is released by pawl 20, the locking pin 23 is able to travel outward. In the operating position of pawl 20, locking pin 23 is in a "ready-to-trip" position. With a fully relaxed spiral spring 18—or in the event of a broken spiral spring 18—the coil 29 of spiral spring 18 presses onto a lug 28 of pawl 20 and may move pawl 20 from the operating position into a locked position, as shown in FIGS. 2 and 3.

Figure 2:
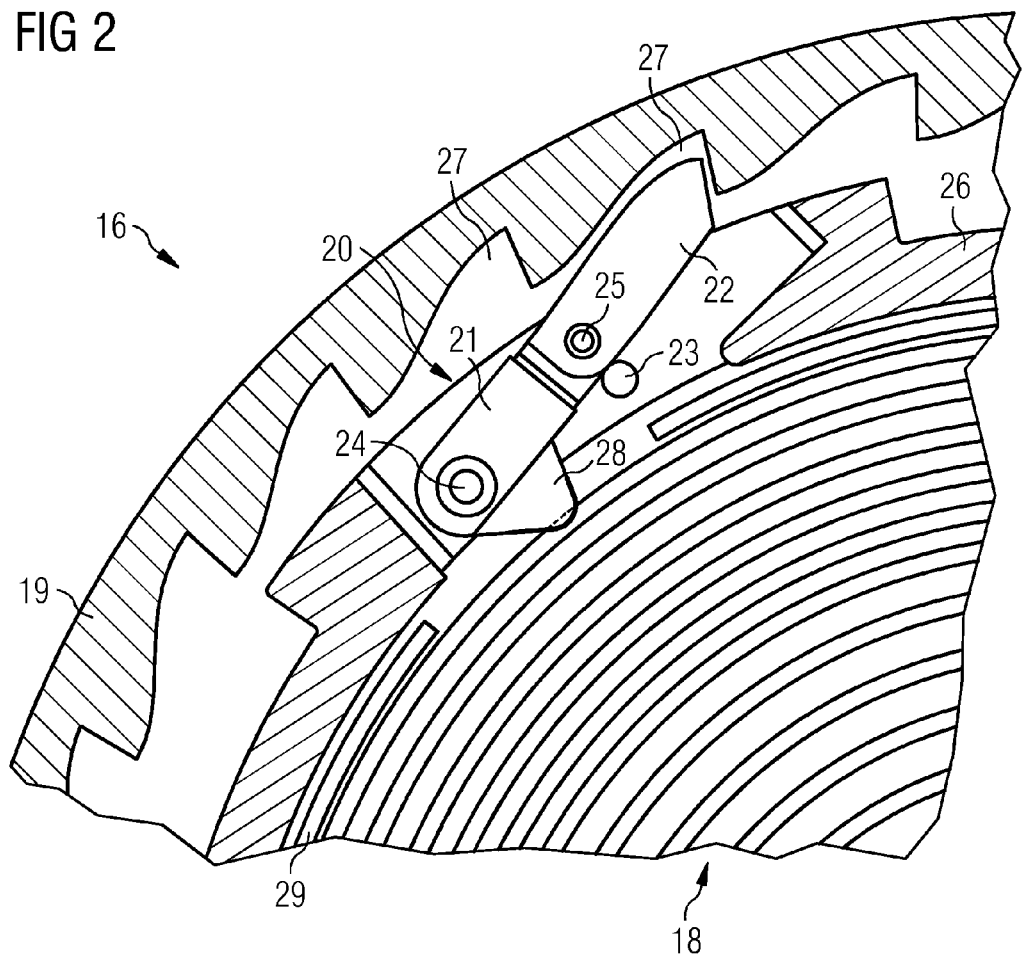
FIG. 2 shows a sectional view of a detail of a representative force compensating device that includes a triggered pawl.

FIG. 2 shows a sectional view of a detail of the representative force compensating device 16 of FIG. 1 in a fault situation. As shown in FIG. 2, the coil 29 of spiral spring 18 is broken. As a result, spiral spring 18 is in a partially relaxed state and presses against the lug 28 of pawl 20, thereby causing pawl 20, which is rotatably connected to the drum 26 about the first axis of rotation 24, to be rotated into a locked position. In the locked position, pawl 20 engages the latching recess 27, thereby preventing further rotation of drum 26 in the clockwise direction. The second element 22 of pawl 20 releases the pretensioned locking pin 23. As a result, locking pin 23 springs upward and, in so doing, blocks a backward rotational movement of pawl 20 (i.e., prevents pawl 20 from accidentally returning to the operating position). The first and second elements 21 and 22 of pawl 20 are connected to each other around the second axis of rotation 25. The pawl 20 is maintained in an extended position by a spring (not shown) at the common center of rotation 25 of the first and second elements 21 and 22.

After the first momentary operation of pawl 20, it is no longer able to return to an initial position (i.e., an operating position) due to locking pin 23. Rather, pawl 20 remains reliably extended in the locking position (i.e., locked position). The outer lying second element 22 is pressed outward by the spring in the second axis of rotation 25, such that pawl 20 may extend straight out without being subject to load, thereby assuring the locking function.

Figure 3:
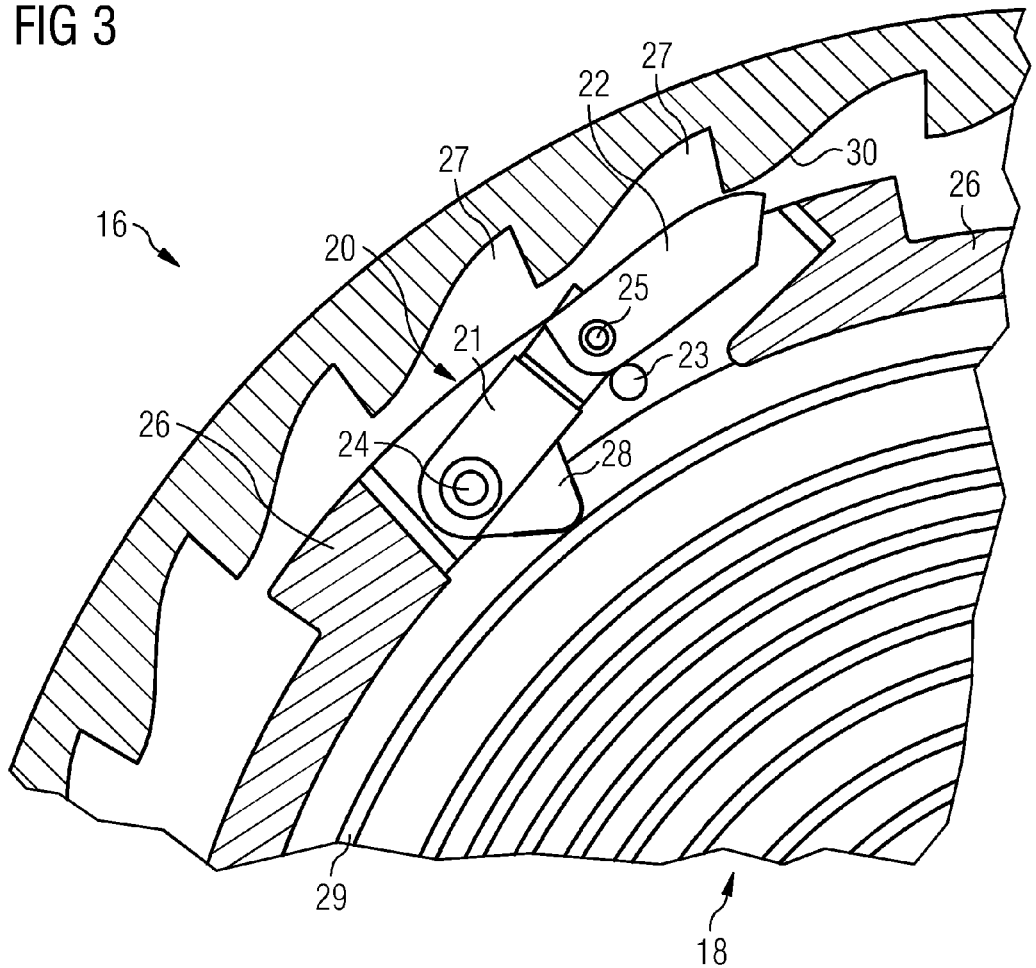
FIG. 3 shows a further sectional view of a representative force compensating device that includes a triggered pawl.

FIG. 3 shows a sectional view of a detail of the representative force compensating device 16 of FIG. 1 in a fault situation. As shown in FIG. 3, the coil 29 of spiral spring 18 presses against the lug 28 of pawl 20, thereby causing pawl 20, which is rotatably connected to drum 26 around the first axis of rotation 24, to be rotated into a locked position. In the locked position, pawl 20 engages latching recess 27, thereby preventing further rotation of drum 26 in the clockwise direction. The first element 21 of pawl 20 releases the pretensioned locking pin 23. As a result, pretensioned locking pin 23 springs upward and, in so doing, blocks a backward rotational movement of the pawl 20 (i.e., prevents pawl 20 from accidentally returning to the operating position).

However, drum 26 may be rotated in the counterclockwise direction. Due to the connectivity of elements 21 and 22, the two-part pawl 20 is able to bend along the second axis of rotation 25. As a result, the second element 22, despite stopping at the locking pin 23, may slide along the rising slope 30 of latching recess 27. FIG. 3 shows the position at which the second element 22 has arrived at the highest point of slope 30. Due to the two-part pawl 20, drum 26 may be rotated in the counterclockwise direction with the application of little force (merely enough to overcome the spring force of the spring in the rotary union of elements 21 and 22 in the second axis of rotation 25.

Thus, safety element 20 triggers reliably even when second element 22 is positioned at a tooth of latching recess 27. Moreover, drum 26 may be moved in one direction in spite of being blocked.

Figure 4:
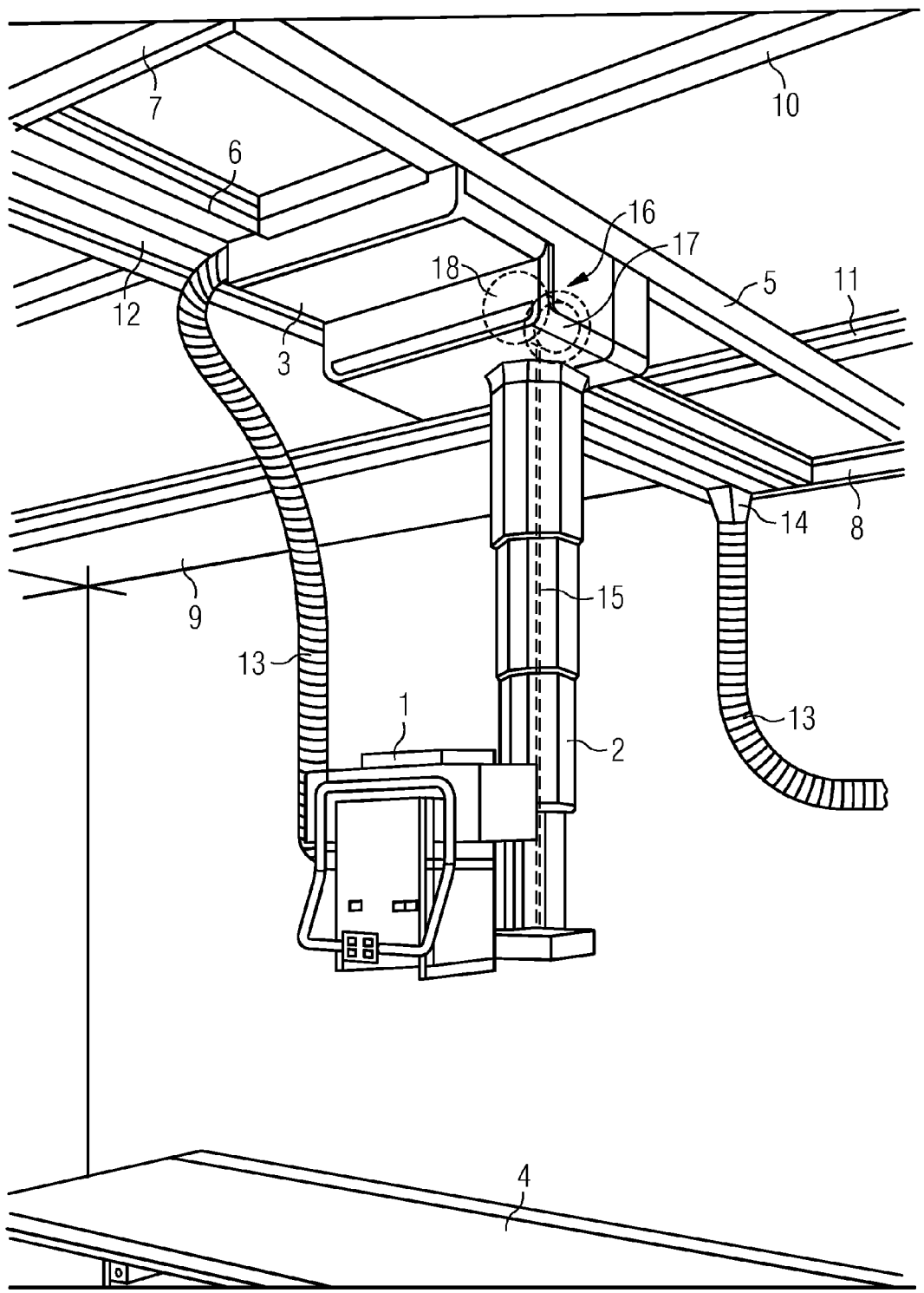
FIG. 4 shows a representative x-ray imaging apparatus.

FIG. 4 shows a representative and non-limiting use of a force compensating device 16 in accordance with the present teachings—namely, its use with a ceiling stand for an x-ray tube assembly 1. As shown in FIG. 4, x-ray tube assembly 1 is mounted on a carriage 3 above an examination table 4 and is adjustable in height by a telescopic column 2. The carriage 3 is displaceable transversely with respect to the examination table 4 by rollers (not shown) along parallel rails 5 and 6. The rails 5 and 6, which are connected to each other by end pieces 7 and 8, are movable by rollers (not shown) along parallel ceiling rails 10 and 11 mounted on a ceiling 9 of the examination room. As shown in FIG. 4, ceiling rails 10 and 11 run at right angles to rails 5 and 6, such that x-ray tube assembly 1 may be moved along the length of examination table 4. A conduit 12 extends parallel to the rail 6 and has a flexible supply cable 13 running through it. The supply cable 13 enters the conduit 12 through a cable feedthrough 14 provided in the vicinity of end piece 8, and exits the conduit 12 in the vicinity of carriage 3 where it is routed to e x-ray tube assembly 1 The feedthrough 14 is stationary with respect to carriage 3.

As shown by the dashed lines in FIG. 4, the x-ray tube assembly 1 is held in position by a supporting cable 15 that runs inside of telescopic column 2 and is attached to the lowest telescopic part thereof. The supporting cable 15 leads to a force compensating device 16 (also shown by dashed lines) which includes, among other components, a cable drum 17 on which supporting cable 15 may be wound and unwound. In some embodiments, supporting cable 15 runs in a spiral groove (not shown) provided on the shell of cable drum 17. In some embodiments, the radius of curvature of the spiral groove varies over its length, such that the weight of the x-ray tube assembly 1 attached to supporting cable 15 is counterbalanced at all times by the force of the force compensating device 16 engaging the cable drum 17. Moreover, the supporting cable 15 is secured to cable drum 17 at one end (not shown). Thus, extremely small forces are sufficient to adjust the height of x-ray tube assembly 1 (viz., forces sufficient to overcome only the friction losses and the inertia of the masses to be moved).

The x-ray tube assembly 1 may still be moved upward even when the safety unit of force compensating device 16 has triggered.

Throughout this description and in the appended claims, the use of an indefinite article (e.g., "a" or "an") before a given element is intended to signify either one or a plurality of the particular element. Solely by way of example, recitations of the phrase "a safety unit" are intended to encompass both a single safety unit as well as a plurality of safety units. Similarly, by way of further example, recitations of the phrase "a locking unit" are intended to encompass both a single locking unit as well as a plurality of locking units.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A force compensating device comprising:
    a force generating unit configured to generate a compensating force to at least partially counteract a tractive force acting on the force compensating device;
    a safety unit coupled to the force generating unit, wherein the safety unit is rotatable about a first axis of rotation, wherein the safety unit comprises a first element and a second element that are rotatably connected to each other at a second axis of rotation, and wherein the safety unit is configured to be moved from an operating position to a locked position by the force generating unit when the force generating unit has a malfunction; and
    a locking unit configured to block movement of the safety unit from the locked position to the operating position when the safety unit is triggered as a result of the malfunction.

2. The force compensating device of claim 1 wherein the safety unit causes the compensating force to be substantially equal to the tractive force when the malfunction occurs.

3. The force compensating device of claim 1 further comprising a latching recess configured for engagement with the safety unit in the locked position.

4. The force compensating device of claim 3 wherein the second element of the safety unit is configured to engage the latching recess.

5. The force compensating device of claim 3 wherein the force generating unit is configured to move the first element of the safety unit about the first axis of rotation, such that the second element is configured to engage the latching recess when the malfunction occurs.

6. The force compensating device of claim 1 wherein the first element of the safety unit is mounted around the first axis of rotation.

7. The force compensating device of claim 6 further comprising a latching recess configured for engagement with the safety unit in the locked position.

8. The force compensating device of claim 7 wherein the second element of the safety unit is configured to engage the latching recess.

9. The force compensating device of claim 7 wherein the force generating unit is configured to move the first element of the safety unit about the first axis of rotation, such that the second element is configured to engage the latching recess when the malfunction occurs.

10. The force compensating device of claim 1 wherein the locking unit is configured to block the second element of the safety unit when the malfunction occurs, thereby preventing the safety unit from returning to the operating position.

11. The force compensating device of claim 1 wherein the force generating unit comprises at least one spring element configured for generating the compensating force.

12. The force compensating device of claim 11 wherein the spring element comprises a spiral spring.

13. The force compensating device of claim 1 wherein the safety unit comprises a two-part pawl.

14. The force compensating device of claim 1 wherein the locking unit comprises a locking pin which, in the operating position of the safety unit, is retained in a triggering position by the safety unit.

15. The force compensating device of claim 3 further comprising a housing having an inside face, wherein the inside face of the housing comprises the latching recess.

16. The force compensating device of claim 1 wherein the tractive force comprises a force exerted due to weight.

17. A force compensating device comprising:
    a force generating unit comprising at least one spring element, wherein the force generating unit is configured to generate a compensating force to at least partially counteract a tractive force acting on the force compensating device;
    a safety unit coupled to the force generating unit, wherein the safety unit is rotatable about a first axis of rotation, wherein the safety unit comprises a first element and a second element that are rotatably connected to each other at a second axis of rotation, and wherein the safety unit is configured to be moved from an operating position to a locked position by the force generating unit when the force generating unit has a malfunction;

a housing having an inside face, wherein the inside face comprises a latching recess, and wherein the latching recess is configured for engagement with the safety unit in the locked position; and a locking unit configured to block movement of the safety unit from the locked position to the operating position when the safety unit is triggered as a result of the malfunction.

18. The force compensating device of claim 17 wherein the spring element comprises a spiral spring.

19. The force compensating device of claim 17 wherein the safety unit comprises a two-part pawl, and wherein the locking unit comprises a locking pin.

20. A method for counterbalancing a component of a medical system, the method comprising:

providing a force compensating device in the medical system, wherein the force compensating device is coupled directly or indirectly to the component, and wherein the force compensating device is configured to counterbalance a force exerted by the component's weight;

wherein the force compensating device comprises:

a force generating unit configured to generate a compensating force to at least partially counteract a tractive force acting on the force compensating device;

a safety unit coupled to the force generating unit, wherein the safety unit is rotatable about a first axis of rotation, wherein the safety unit comprises a first element and a second element that are rotatably connected to each other at a second axis of rotation, and wherein the safety unit is configured to be moved from an operating position to a locked position by the force generating unit when the force generating unit has a malfunction; and a locking unit configured to block movement of the safety unit from the locked position to the operating position when the safety unit is triggered as a result of the malfunction.

\* \* \* \* \*